(12) United States Patent
Sra

(10) Patent No.: US 7,270,669 B1
(45) Date of Patent: Sep. 18, 2007

(54) EPICARDIAL LEAD PLACEMENT FOR BI-VENTRICULAR PACING USING THORACOSCOPIC APPROACH

(75) Inventor: Jasbir S. Sra, Pewaukee, WI (US)

(73) Assignee: Medtronic, Inc., Minneapolis, MN (US)

( * ) Notice: Subject to any disclaimer, the term of this patent is extended or adjusted under 35 U.S.C. 154(b) by 573 days.

(21) Appl. No.: 10/379,946

(22) Filed: Mar. 5, 2003

Related U.S. Application Data

(60) Provisional application No. 60/364,311, filed on Mar. 14, 2002.

(51) Int. Cl.
*A61B 17/94* (2006.01)
*A61N 1/05* (2006.01)

(52) U.S. Cl. .................. 606/129; 607/131; 600/375
(58) Field of Classification Search ............ 600/375; 606/129; 607/129–131
See application file for complete search history.

(56) References Cited

U.S. PATENT DOCUMENTS

| | | | | |
|---|---|---|---|---|
| 3,737,579 | A | * | 6/1973 | Bolduc ................ 607/131 |
| 3,875,947 | A | * | 4/1975 | Jula et al. ............ 607/131 |
| 4,010,758 | A | * | 3/1977 | Rockland et al. ..... 607/131 |
| 4,146,037 | A | * | 3/1979 | Flynn et al. ......... 607/131 |
| 4,271,846 | A | * | 6/1981 | Little .................. 607/131 |
| 4,280,510 | A | * | 7/1981 | O'Neill ............... 607/131 |
| 4,972,847 | A | * | 11/1990 | Dutcher et al. ...... 607/131 |
| 5,391,200 | A | * | 2/1995 | KenKnight et al. ... 607/129 |
| 5,464,447 | A | | 11/1995 | Fogarty et al. |
| 5,829,447 | A | | 11/1998 | Stevens et al. |
| 5,846,254 | A | | 12/1998 | Schulze et al. |
| 5,871,530 | A | * | 2/1999 | Williams et al. ..... 607/122 |
| 5,871,532 | A | | 2/1999 | Schroeppel |

(Continued)

FOREIGN PATENT DOCUMENTS

SU 1410991 * 7/1988

OTHER PUBLICATIONS

Grines CL, et al. Functional abnormalities in Isolated LBBB; the effect of interventricular asynchrony. Circulation 1989;79:845-53.
A report of the American College of Cardiology/American Heart Association Task Force on Practice Guidelines (ACC/AHA/NASPE 2002 Guidelines Update for Impolantation of Cardiac Pacemakers and Antiarrhythythmia Devices. American College of Cardiology website 2002.

(Continued)

*Primary Examiner*—Kristen Droesch Mullen
(74) *Attorney, Agent, or Firm*—Jansson Shupe & Munger Ltd.

(57) ABSTRACT

A method and apparatus for placing an epicardial lead over a desired, predetermined location on the left ventricle using a minimally invasive approach. A thoracoscope having a handle portion and a probe tube defining a central opening is placed through an incision in the patient generally aligned with the desired position for the pacing lead. An introducer and pacing lead are placed within the central opening of the thoracoscope and moved into contact with the pericardium at the desired lead location. An attachment member of the pacing lead attaches an electrode of the pacing lead to the pericardium. The pacing lead includes a mesh disk surrounding the electrode to aid in long term attachment of the electrode to the heart. Alternatively, the pericardium can be incised such that the lead is placed directly over the epicardial surface of the left ventricle.

18 Claims, 4 Drawing Sheets

U.S. PATENT DOCUMENTS

| | | | |
|---|---|---|---|
| 5,931,849 A * | 8/1999 | Desvignes et al. | 606/167 |
| 5,954,692 A | 9/1999 | Smith et al. | |
| 6,079,414 A | 6/2000 | Roth | |
| 6,234,804 B1 | 5/2001 | Yong | |
| 6,311,693 B1 | 11/2001 | Sterman et al. | |
| 6,348,034 B1 | 2/2002 | Thompson | |
| 6,350,248 B1 | 2/2002 | Knudson et al. | |
| 6,394,948 B1 | 5/2002 | Borst et al. | |
| 6,401,720 B1 | 6/2002 | Stevens et al. | |
| 6,423,051 B1 | 7/2002 | Kaplan et al. | |
| 6,478,028 B1 | 11/2002 | Paolitto et al. | |
| 6,478,803 B1 | 11/2002 | Kapec et al. | |
| 6,520,953 B1 | 2/2003 | Schultz | |
| 6,606,113 B2 | 8/2003 | Nakamura | |
| 6,612,980 B2 | 9/2003 | Chen et al. | |
| 6,614,595 B2 | 9/2003 | Igarashi | |
| 2003/0074041 A1 * | 4/2003 | Parry et al. | 607/130 |
| 2003/0130571 A1 * | 7/2003 | Lattouf | 600/374 |

OTHER PUBLICATIONS

Xiao HB, et al. Differing effects of right ventricular pacing and LBBB on left ventgricular function. Br Heart J 1993;69:166-73.

Cazeau S, et al. the MUltisite Stimulation in Cardiomyopathies (MUSTIC) Study Investigators, Effect of multisite biventricular pacing in patients with heart failure and intraventricular conduction delay. N engl J. Med 2001;344:873-880.

Pitzalis MV, et al. Cardiac resynchronization therapy tailored by echocardiographic evaluation of ventricular asynchrony. J Am Coll Cardiol 2002;40:1615-22.

Abraham WT, et al. for the MIRACLE study group. Cardiac resynchronization in chronic heart failure. N Engl J Med 2002; 346:1845-1853.

* cited by examiner

EPICARDIAL LEAD PLACEMENT FOR BI-VENTRICULAR PACING USING THORACOSCOPIC APPROACH

CROSS REFERENCE TO RELATED APPLICATION

The present invention is based on and claims priority to U.S. Provisional Patent Application Ser. No. 60/364,311 filed on Mar. 14, 2002.

FIELD OF THE INVENTION

The present invention, called "stingray technique", generally relates to a technique of inserting an epicardial lead in a patient with congestive heart failure (CHF) requiring bi-ventricular pacing. More specifically, the present invention is related to a thoracoscope design and technique of inserting a left ventricular lead using an thoracoscopic approach that places the lead at a specific, known location on the epicardial surface of the left ventricle.

BACKGROUND OF THE INVENTION

Despite considerable progress in the management of CHF, it remains a major health problem worldwide. It is estimated that there are 6-7 million people with CHF in the United States and Europe alone and approximately 1 million new patients are diagnosed with CHF every year.

Despite significant advances in the treatment of CHF using various pharmacological therapies, the quality-of-life in patients with CHF remains poor as these patients are frequently hospitalized, and heart failure in these patients is a common cause of death. In addition, there are significant long-term care costs associated with this problem.

Many patients with advanced CHF have a conduction system disease that may play a role in worsening cardiac function. One frequently noted conduction abnormality is left bundle branch block (LBBB), which is present in about 29% of patients with CHF. The presence of LBBB delays left ventricular ejection due to delayed left ventricular activation.

Pacing therapies have been introduced in an attempt to improve cardiac function in patients diagnosed with CHF. Cardiac resynchronization, in which bi-ventricular pacing is performed, has shown beneficial results in patients with CHF and LBBB. During bi-ventricular pacing, in addition to the standard right atrial and right ventricular leads, an additional lead is positioned in the coronary sinus. This additional lead is advanced into one of the branches of the coronary sinus overlaying the epicardial surface of the left ventricle. Since the lead is advanced through the coronary sinus, the potential placement positions for the lead are severely limited.

Although bi-ventricular pacing has shown beneficial results, numerous problems are associated with this technique. One such problem is the amount of time required for a physician to insert the lead into the desired location on the left ventricle. Further, the placement of the lead on the left ventricle is limited to sites that provide adequate pacing and sensing signals. Further, cannulation of the coronary sinus is often difficult due to either the rotation of the heart or the presence of an enlarged right atrium or Thebesian valve. Further, the placement of a lead on the surface of the left ventricle though the coronary sinus cannot be carried out in some patients with prior bypass surgery or with coronary sinus stenosis. Finally, the coronary sinus lead provides an oftentimes unstable placement and can become detached after installation.

Therefore, a need exists for an alternative approach that allows for the easier placement of the left ventricle lead and an apparatus for positioning such a lead in the desired location.

SUMMARY OF THE INVENTION

The present invention is directed to a method and apparatus for placing an epicardial pacing lead on the left ventricle using a minimally invasive approach.

A thoracoscope is provided including a handle portion and a hollow probe tube that extends from the handle portion such that the handle portion and the probe tube define a central opening extending along a longitudinal axis. Preferably, a camera and a light source can be positioned through the central opening such that the camera can provide images relating to the placement of the thoracoscope within the chest cavity.

The apparatus of the present invention further includes an introducer that is configured for receipt in the central opening of the thoracoscope. The introducer includes a hollow body portion that extends from a proximal end to a distal end. The introducer is movable along the longitudinal axis of the thoracoscope such that the distal end of the introducer can project varying distances from the probe tube. During a lead placement procedure, the distal end of the introducer is brought into contact with the pericardium surrounding the heart for proper lead delivery.

A pacing lead having an electrode coupled to a lead wire is positioned within the introducer and is movable along the longitudinal axis of the introducer. The pacing lead includes an electrode surrounded by a mesh disk. The pacing lead further includes an attachment member, such as a screw-like wire, for use in securing the electrode in contact with the desired location on the pericardium. Preferably, the pacing lead is movable along the longitudinal axis of the introducer such that the electrode and mesh disk are movable between a retracted position in which the electrode and mesh disk are contained within the distal end of the introducer and an extended position in which the electrode and mesh disk extend from the distal end of the introducer.

The method of placing the pacing lead in contact with the pericardium initially requires the right ventricular lead and the right atrial lead to be placed on the heart in the usual manner. Once the two leads have been placed, the patient is placed on his or her back and the procedure begins. Initially, a double-lumen endotracheal tube is used to selectively ventilate the patient's right lung while blocking ventilation of the left lung to create space in the left pleural cavity. Once the required space is created, a small incision is made in the left fifth intercostal space or another appropriate site to allow placement of a thoracic port to maintain access to the left pleural cavity. Prior to the incision, an imaging system, such as CT or MR is used to determine the proper lead placement on the epicardial surfaces of the left ventricle. The proper lead placement is the determined location on the epicardial surface of the left ventricle that will provide the optimal delivery point for an electrical signal to aid in heart pacing. Although CT and MR are known techniques for obtaining such images, other imaging techniques are contemplated.

Once the incision is made, the probe tube of the thoracoscope is introduced through the port and the left ventricle is visualized using a camera and light source introduced through the thoracoscope. The vessels, fat and phrenic nerve are identified using images received from the thoracoscope.

Once the probe tube is properly positioned, the introducer including the retracted epicardial lead, is introduced into the probe tube and extended to the desired position over the pericardium. Once the introducer is properly placed, the lead is extended from the distal end of the introducer. The lead is then rotated such that the screw-like attachment member of the pacing lead penetrates the pericardium over the desired location on the epicardium. If it is not possible to attach the lead directly to the pericardium and deliver the proper pacing signal to the left ventricle, the pericardium can be incised and opened to provide access directly to the epicardial surface of the left ventricle.

Once the lead has been anchored in place by the attachment member, the thoracoscope and introducer are removed and tests done to confirm the desired location of the lead. It is contemplated that more than one lead can be placed during the procedure in order to provide a redundant system.

Once the thoracoscope has been removed, the lead is tunneled to the left pectoral pocket with the remaining leads and connected to the pacemaker.

Various other features, objects and advantages of the invention will be made apparent from the following description taken together with the drawings.

BRIEF DESCRIPTION OF THE DRAWINGS

The drawings illustrate the best mode presently contemplated of carrying out the invention.

In the drawings.

DETAILED DESCRIPTION OF THE INVENTION

Figure 1:
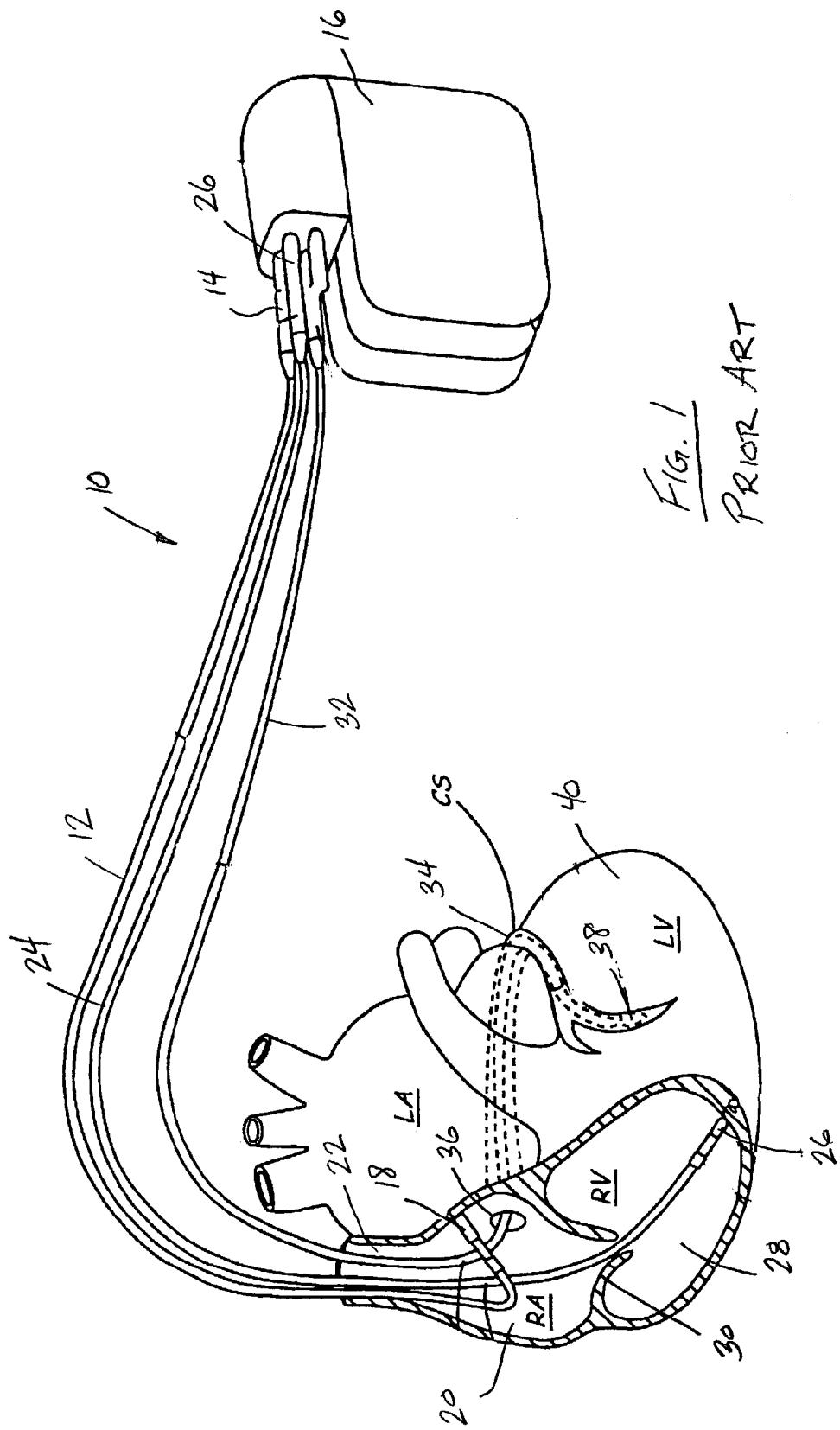
FIG. 1 is a schematic illustration of the standard transvenous leads placed in the right atrium (RA), right ventricle (RV) and the coronary sinus (CS)

Referring first to FIG. 1, thereshown is a schematic illustration of a prior art bi-ventricular pacing method and apparatus 10 currently used. The bi-ventricular pacing system 10 shown in FIG. 1 utilizes a totally transvenous lead system. Specifically, a right atrial lead 12 has one end 14 connected to a pacemaker 16 and a distal end including an electrode 18 in contact with the inner wall of the right atrium 20. As illustrated in FIG. 1, the right atrial lead 12 is fed into the heart through the superior vena cava 22.

A second, right ventricular lead 24 is coupled at its end 26 to the pacemaker 16 and its distal end, including a electrode 26 is placed in contact with the inner wall of the right ventricle 28. The right ventricular lead 24 also passes through the vena cava 22 and passes through the tricuspid valve 30. The third lead 32 of the pacing system 10 passes through the vena cava 22 and enters into the coronary sinus 34 through the opening 36 in the right atrium 20. The third lead 32 is fed through the coronary sinus and includes an electrode 38 positioned in contact with the outer surface of the left ventricle 40 through the coronary sinus. As described previously, the placement of the third lead 32 in the coronary sinus 34 presents both a time-consuming and difficult task to a physician. Additionally, placement of the lead in the coronary sinus 34 is difficult in many cases due to the rotation of the heart and in the presence of an enlarged right atrium or Thebesian valve. Further, patients who have had prior bypass surgery or have coronary sinus stenosis are not candidates for total transvenous lead system incorporating the lead 32 within the coronary sinus 34.

In the pacing system 10 illustrated in FIG. 1, sensing of the heart rhythm occurs in the electrode 18 of the right atrial lead 12. The pacemaker 16 paces the heart through the right atrial lead 12 followed by synchronized pacing between the right ventricular lead 24 and the coronary sinus lead 32. The synchronized pacing results in narrowing of the QRS complex of the heart rhythm in a known and conventional manner. Although the total transvenous lead pacing system 10 of the prior art shown in FIG. 1 has proven effective, problems exist in placing the lead in the coronary sinus.

Figure 2:
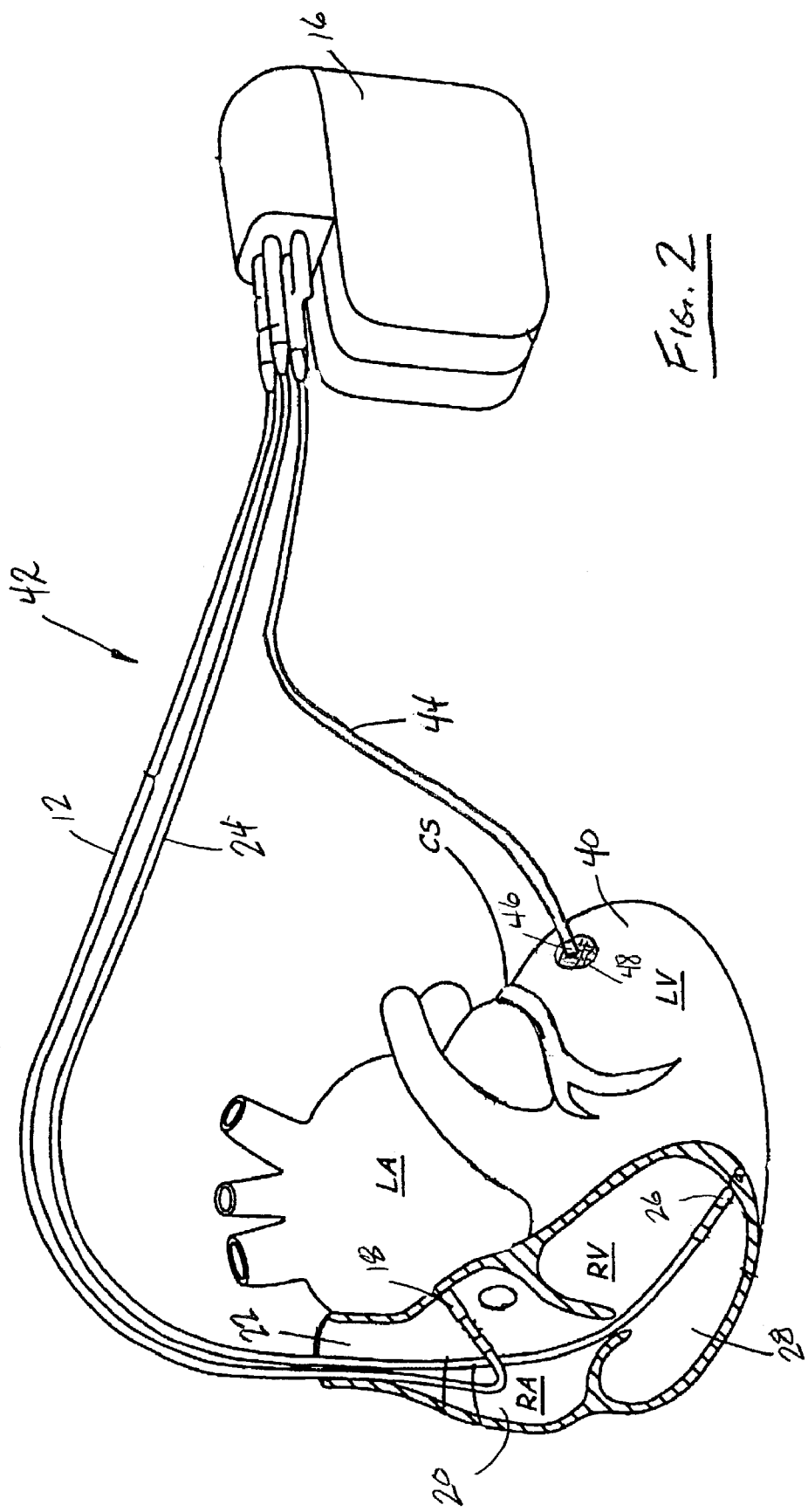
FIG. 2 is a schematic illustration similar to FIG. 1 illustrating the transvenous lead placement in the right atrium, right ventricle, and the epicardial lead placement on the left ventricle using the method and technique of the present invention.

Referring now to FIG. 2, thereshown is the pacing system 42 of the present invention. As illustrated, the pacing system 42 includes the pacemaker 16 and both the right atrial lead 12 and the right ventricular lead 24. The right atrial lead 12 includes the electrode 18 in contact with the wall of the right atrium 20 and the right ventricular lead 24 includes electrode 26 in contact with the wall of the right ventricle 28. However, in accordance with the present invention, the third coronary sinus lead is replaced with a left ventricular lead 44 that, instead of passing through the superior vena cava 22, is attached directly to the epicardial surface of the left ventricle 40. The left ventricular lead 44 includes an electrode 46 held in contact with the epicardial surface by a mesh pad 48 and an attachment member (not shown) such that the required electrical signals can be transferred to the left ventricle 40.

Traditionally, the left ventricular lead 44 is placed in contact with the pericardium during thoracotomy in which part of the pericardium is excised to expose the epicardium. Once the epicardium has been exposed, the electrode 46 of the left ventricular lead 44 is placed at the site as appropriate. In the prior art methods of placing the left ventricular lead 44, only a limited view of the left ventricle is obtained and, because the patient must be tilted sideways to make thoracotomy easier, the left ventricle 40 is somewhat rotated, making it more difficult to position the left ventricular lead 44 in the posterolateral region of the left ventricle.

In an attempt to address the problems associated with the placement of the left ventricular lead 44 during thoracotomy, the present invention utilizes a thoracoscopic approach to facilitate the left ventricular lead placement. The present invention eliminates the flaws in the current technique of epicardial left ventricular lead placement during thoracotomy and improves the efficacy of this approach.

Figure 3:
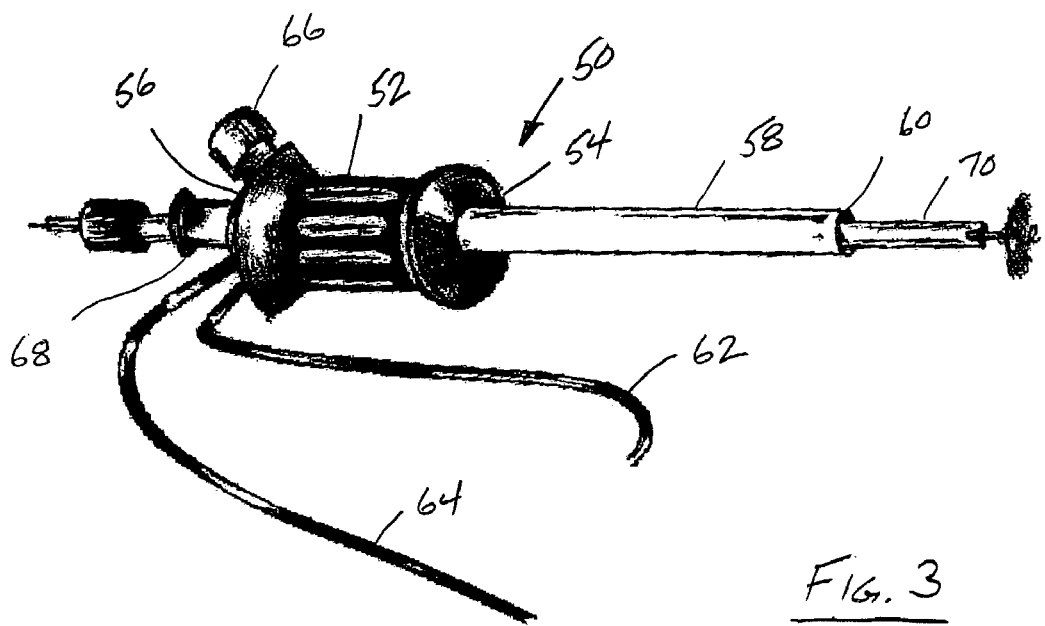
FIG. 3 is a perspective view of the epicardial lead placement apparatus of the present invention including a thoracoscope, introducer and an epicardial pacing lead of the present invention.

Referring now to FIG. 3, thereshown is a thoracoscope 50 constructed in accordance with the present invention. The thoracoscope 50 includes a hollow handle portion 52 having an inner end 54 and an outer end 56. The thoracoscope 50 includes a hollow probe tube 58 extending from the inner end 54 of the handle portion 52 to a distal end 60. In the preferred embodiment of the invention, the probe tube 58 has a hollow, open interior and is formed from a rigid material such that the probe tube 58 can be inserted through an incision in the patient. The probe tube 58 extends along a generally longitudinal axis and defines a central opening along the longitudinal axis that extends through both the probe tube 58 and the handle portion 52 of the thoracoscope 50.

The outer end 56 of the handle portion 52 is designed to receive both a light source 62 and a camera 64 which can be fed through the probe tube 58 to the distal end 60. The camera 64 and light source 62 allow images to be displayed in real time such that the physician can monitor the procedure through a display device, such as a video monitor.

The handle 52 further includes an irrigation port 66 that helps irrigate and aspirate the thoracoscope as needed. The irrigation port 66 is connected to a supply of irrigation fluid, as is conventional.

The handle portion 52 of the thoracoscope 50 includes an extended tube 68 having a hollow interior centered along the longitudinal axis of both the probe tube 58 and the handle portion 52. Thus, the probe tube 58, handle portion 52 and extended tube 68 are all coaxial with each other to define a continuous central opening through the thoracoscope 50.

Figure 5:
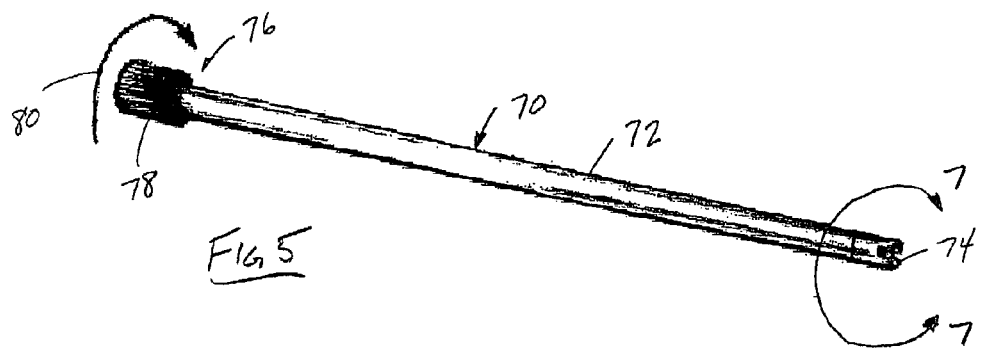
FIG. 5 is a perspective view of the introducer used with the thoracoscope of the present invention.

Referring now to FIGS. 3 and 5, the thoracoscope is sized to receive an introducer 70. The introducer 70 includes a hollow, tubular body portion 72 that extends from a distal end 74 to a proximal end 76. The proximal end 76 includes a handle portion 78 having a series of external grooves that allow the introducer 70 to be rotated along its longitudinal axis, as illustrated by arrow 80 in FIG. 5. In the preferred embodiment of the invention, the body portion 72 of the introducer 70 has a circular cross-section that slightly tapers from the proximal end 76 to the distal end 74. Preferably, the outer surface of the body portion includes a matte black non-reflective surface such that light from the light source 62 does not interfere with the lead positioning, as will be described in detail below.

Figure 7:
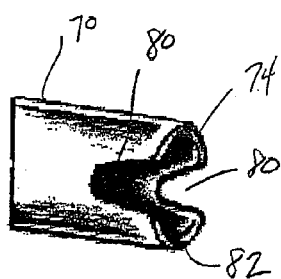
FIG. 7 is a magnified view of the distal end of the introducer as viewed along line 7-7 of FIG. 5.

Referring now to FIG. 7, the distal end 74 of the introducer 70 is open and includes a pair of notches 80 recessed from an outer rim 82. In the preferred embodiment of the invention, the distal end 74 of the introducer 70 is formed from a somewhat flexible material such that the distal end 74 can be placed into contact with the pericardium of the heart without damaging such surface.

Figure 4:
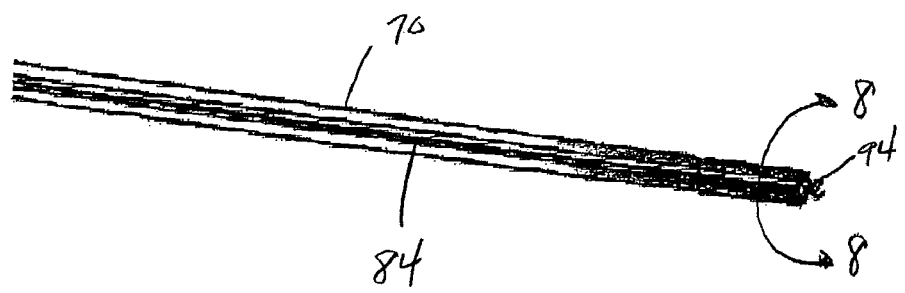
FIG. 4 is a perspective view of the introducer with the lead contained therein.

Referring now to FIG. 4, the hollow introducer 70 includes a hollow, open interior that generally is coaxial with the hollow interior of the probe tube 58 and is sized to receive an epicardial pacing lead 84. The epicardial pacing lead 84 extends through the hollow interior of the introducer 70 and is movable along the longitudinal axis of the introducer 70.

Figure 6:
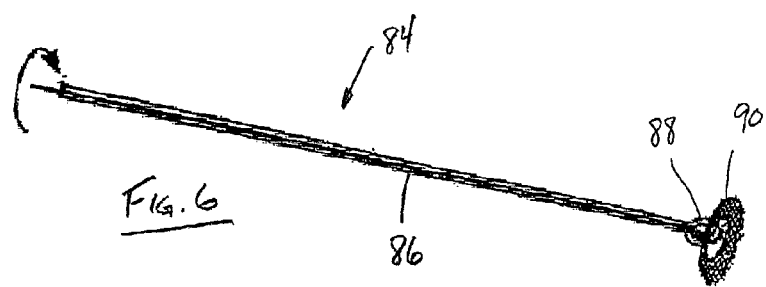
FIG. 6 is a perspective view of the epicardial pacing lead of the present invention.

Referring now to FIG. 6, the epicardial pacing lead 84 includes a wire 86 coupled to an electrode 88. The electrode 88 is centered within a mesh disk 90. The electrode 88 is coupled to the wire 86, which in turn is connected at its opposite end to the pacemaker 16, as shown in FIG. 2. Preferably, the outer surface of the wire 86 includes a matte black non-reflective surface such that light from the light source does not interfere with the lead positioning, as will be described in detail below.

Referring back now to FIG. 8b, when the distal end 92 of the epicardial pacing lead 84 is extended from the distal end 74 of the introducer 70, the mesh disk 90 extends outward and surrounds the electrode 88. In the preferred embodiment of the invention, the mesh disk 90 is formed from a resilient material that has a pre-formed shape, as shown. When the mesh disk 90 is extended from the distal end 74 of the introducer 72, the mesh disk 90 extends to the configuration shown.

Figure 8A:
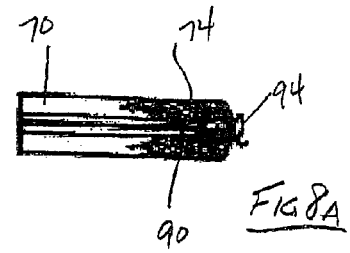
FIG. 8a is a magnified view taken along line 8-8 of FIG. 4 illustrating the distal end of the introducer with the electrode of the epicardial pacing lead contained therein.
Figure 8B:
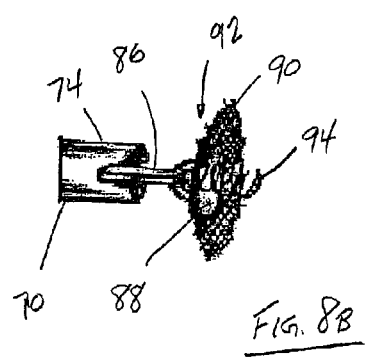
FIG. 8b is a magnified view taken along line 8-8 of FIG. 4 illustrating the protrusion of the electrode of the epicardial pacing lead extending from the distal end of the introducer.

The electrode 88 includes a screw-like attachment member 94 that is used to hold the electrode 88 in contact with the pericardium after placement of the epicardial pacing lead 84. As illustrated in FIG. 8a, before the epicardial pacing lead 84 is extended, the mesh disk 90 is compressed within the introducer 70 and the attachment member 94 extends slightly from the distal end 94. As can be understood in FIGS. 8a and 8b, the epicardial pacing lead 84 is movable longitudinally along the central axis of the introducer 70 to extend and retract the electrode 88 as desired.

Although a specific embodiment of the lead and electrode are shown in the Figures of the present invention, it should be understood that other designs and configurations for the lead and electrode 88 are contemplated as being within the scope of the present invention.

The procedure for attaching the left ventricular lead 44 using the method and apparatus of the present invention will now be described. Initially, the patient is positioned in a supine position prior to performance of the procedure. With the patient positioned correctly, a double lumen endotracheal tube is inserted to ventilate the right lung while at the same time ventilation is blocked to the left lung to create a space in the left pleural cavity. With the left lung deflated, a small incision is made with a scalpel at the sight identified as adjacent to the left ventricle sight considered most appropriate for left ventricular lead placement. The identification of the desired sight on the left ventricle can be done using various imaging techniques, such as computerized tomography.

Once the desired location on the left ventricle is determined, a small 4-5 mm, 3-4 cm long thoracic port is placed over the incision and anchored in place. The thoracic port helps maintain the intercostal space, decreases trauma and maintains pleural access.

Once the thoracic port is positioned correctly, the probe tube 58 of the thoracoscope 50 of the present invention is introduced through the thoracic port. The camera 64 and light source 62 of the thoracoscope 50 are used to verify the lack of left lung ventilation and to identify intrapleural and mediastinal anatomies.

Once the probe tube 58 of the thoracoscope 50 is properly positioned, the introducer 70 including the epicardial pacing lead 84 is inserted into the probe tube 50 through the extended tube 68 and handle portion 52. With the introducer 70 extending through the probe tube 58, the appropriate left ventricle sight, which is devoid of blood vessels, is identified. Additionally, the phrenic nerve can also be identified at this time through use of the thoracoscope 50.

Once the appropriate left ventricle sight is identified, the introducer 70 and the epicardial pacing lead 84 are advanced into contact with the pericardium at the appropriate site. Pressure is placed against the pericardium and, with pressure against the heart, the attachment member 94 of the lead is screwed through the pericardium until the mesh disk 90 contacts the outer surface of the pericardium. Once positioned, the lead is tested to determine whether adequate pacing is achieved.

If adequate pacing is not achieved, a small nick is made in the pericardium to expose the epicardial surface. If the pericardium needs to be split for epicardial lead placement, a pericardial holding and incising device (not shown) can be introduced through the introducer 70. Once the pericardium has been nicked, the lead is positioned directly in contract with the pericardium and pacing thresholds performed to determine stability and the appropriateness of lead location. During this portion of the procedure, more than one lead can be placed in order to provide a redundant system.

Once the appropriate lead location on the left ventricle has been identified and the thoracoscope removed, the lead is tunneled to the left pectoral region where a pocket has been created to position the pacemaker 16 or other implantable defibrillator. A suction tube for expansion of the lung can be placed through the same incision if required. Additionally, other leads could be implanted using the same technique and tunneled to the left pectoral pocket if required.

While the present invention has been described with reference to bi-ventricular pacing in patients with CHF, it should be understood that the method and apparatus of the present invention could be utilized in other conditions such as children with heart blocks who may need pacing because a transvenous approach is suboptimal due to the complications associated with growth. Different lead designs and different sizes of thoracoscopes including disposable units may also be used while operating within the scope of the present invention.

In addition, although the invention has been described with reference to its exemplary embodiments, it should be understood by those skilled in the art that various changes may be made without departing from the scope of the invention. In addition, change and modifications may be made in order to adapt a particular situation or material without departing from the essential scope thereof. Therefore, it is intended that the invention not be limited to the particular embodiment disclosed as the best mode for carrying out the invention, but that the invention will include all embodiments falling within the scope of the appended claims.

It is contemplated by the inventor that a registration and imaging process may be used in which appropriate sites for pacing obtained by imaging techniques, such as CT or MR could be used for placement of leads. Once the appropriate sites are identified, it may be possible to place a lead without the need of an endoscope. Additional navigational tools may be used to position the lead at the appropriate site.

I claim:

1. A method of placing a pacing lead in contact with an epicardial surface of a left ventricle of a patient's heart for delivering an electric signal thereto, the method comprising the steps of:
    identifying a desired placement position for the pacing lead on the epicardial surface of the patient's heart using an external imaging system;
    creating an incision in the patient above the patient's left pleural cavity and generally aligned with the desired pacing lead placement position;
    providing a thoracoscope having a handle portion and a rigid hollow probe tube adapted for viewing throughout a chest cavity of the patient extending from the handle, the thoracoscope having a central opening extending along a longitudinal axis through the handle portion and the probe tube;
    inserting the probe tube through the incision;
    inserting an introducer into the central opening of the thoracoscope, the introducer having a hollow body extending from a proximal end to a distal end;
    inserting the pacing lead into the introducer, the pacing lead having an electrode for delivering the electric signal and a mesh disk surrounding the electrode, the pacing lead being inserted into the introducer such that the electrode and the mesh disk are received within the distal end of the introducer;
    moving the introducer along the longitudinal axis of the thoracoscope until the distal end of the introducer contacts a surface of a pericardium of the heart at the desired lead placement position;
    moving the pacing lead along the longitudinal axis until the electrode and the mesh disk extend from the distal end of the introducer and into contact with the pericardial surface of the heart, the mesh disk returning to a pre-formed orientation; and
    securing the electrode to the epicardial surface of the heart.

2. The method of claim 1 wherein the pacing lead includes an attachment member having a screw-like configuration, wherein the step of securing the electrode to the epicardial surface includes rotating the pacing lead such that the screw-like attachment member screws through the pericardial surface into the epicardial surface.

3. The method of claim 1 further comprising the step of creating a small incision in the pericardium prior to attaching the lead to the epicardial surface, the incision exposing the epicardial surface without removing any portion of the pericardium.

4. The method of claim 1 further comprising the step of introducing a camera and a light source into the thoracoscope to obtain images through the thoracoscope.

5. An apparatus for placing a lead in contact with an epicardium of a left ventricle of a patient, the apparatus comprising:
    a thoracoscope including a handle portion and a hollow probe tube extending from the handle portion, the thoracoscope having a central opening extending along a longitudinal axis through the handle portion and the probe tube;
    an introducer configured for receipt in the central opening, the introducer having a hollow body portion extending from a proximal end to a distal end, the distal end projecting from the probe tube when the introducer is received in the thoracoscope, wherein the introducer is movable along the longitudinal axis and rotatable about the longitudinal axis; and
    a pacing lead configured for receipt in the introducer, the pacing lead having an electrode coupled to a lead wire for delivering an electric signal to the epicardium, the pacing lead including a mesh disk surrounding the electrode and an attachment member for securing the electrode to the epicardium, wherein the pacing lead is movable along the longitudinal axis such that the electrode and the mesh disk are movable between a retracted position in which the electrode and mesh disk are contained within the distal end of the introducer and an extended position in which the electrode and mesh disk extend from the distal end of the introducer.

6. The apparatus of claim 5 wherein the attachment member is a wire having a screw-like configuration, wherein the pacing lead is secured to the epicardium by rotating the pacing lead relative to the epicardium to screw the attachment member into the epicardium.

7. The apparatus of claim 5 wherein the mesh disk is formed from a resilient material having a pre-formed orientation such that the mesh disk is compressible to be received within the distal end of the introducer and such that the mesh disk assumes the pre-formed orientation when the mesh disk is extended from the distal end of the introducer.

8. The apparatus of claim 5 wherein the distal end of the introducer is formed from a flexible material such that the distal end of the introducer can be brought into contact with the epicardium.

9. The apparatus of claim 5 wherein the thoracoscope further comprises a light source and a camera positioned to obtain images through a probe tube of the thoracoscope.

10. An apparatus for placing a lead in contact with an epicardium of a patient, the apparatus comprising:
- a thoracoscope including a handle portion and a hollow probe tube extending from the handle portion, the thoracoscope having a central opening extending along a longitudinal axis through the handle portion and the probe tube;
- an introducer received within the central opening of the thoracoscope, the introducer having a hollow body portion extending from a proximal end to a distal end, wherein the introducer is movable along the longitudinal axis; and
- the lead received within the introducer, the lead having an electrode coupled to a lead wire for delivering an electric signal, a mesh disk having a preformed orientation surrounding the electrode, wherein the lead is movable within the introducer along the longitudinal axis such that the electrode is movable between a retracted position in which the electrode and mesh disk are contained within the distal end of the introducer and an extended position in which the electrode and mesh disk extend from the distal end of the introducer.

11. The apparatus of claim 10 wherein the pacing lead further comprises an attachment member for securing the pacing lead to the epicardium.

12. The apparatus of claim 11 wherein the attachment member is a wire having a screw-like configuration, wherein the pacing lead is secured to the epicardium by rotating the lead relative to the introducer to screw the attachment member through a pericardium into the epicardium.

13. The apparatus of claim 10, wherein the mesh disk is formed from a resilient material such that when the mesh disk is extended from the distal end of the introducer, the mesh disk assumes the pre-formed orientation.

14. The apparatus of claim 10 wherein the distal end of the introducer projects outward from the probe tube and is formed from a flexible material such that the distal end of the introducer can be placed in contact with the epicardium.

15. The apparatus of claim 10 wherein the thoracoscope further includes a light source and a camera mounted thereto adapted to obtain images through the probe tube.

16. The apparatus of claim 10 wherein the probe tube, handle, introducer and lead are all coaxial.

17. The apparatus of claim 10 wherein the lead wire of the lead includes a non-reflective outer surface.

18. The apparatus of claim 10 wherein the body portion of the introducer includes a non-reflective outer surface.

* * * * *

UNITED STATES PATENT AND TRADEMARK OFFICE
CERTIFICATE OF CORRECTION

| | |
|---|---|
| PATENT NO. | : 7,270,669 B1 |
| APPLICATION NO. | : 10/379946 |
| DATED | : September 18, 2007 |
| INVENTOR(S) | : Jasbir S. Sra |

Page 1 of 1

It is certified that error appears in the above-identified patent and that said Letters Patent is hereby corrected as shown below:

Claim 11:
    Column 10, line 5, delete "pacing".
    Column 10, line 7, delete "pacing".

Claim 12:
    Column 10, line 10, delete "pacing".

Signed and Sealed this

Eighteenth Day of December, 2007

JON W. DUDAS
*Director of the United States Patent and Trademark Office*

UNITED STATES PATENT AND TRADEMARK OFFICE
CERTIFICATE OF CORRECTION

PATENT NO. : 7,270,669 B1  
APPLICATION NO. : 10/379946  
DATED : September 18, 2007  
INVENTOR(S) : Jasbir S. Sra It is certified that error appears in the above-identified patent and that said Letters Patent is hereby corrected as shown below:

Claim 11:
    Column 10, line 5, delete "pacing".
    Column 10, line 7, delete "pacing".

Claim 12:
    Column 10, line 10, delete "pacing".

Signed and Sealed this

First Day of January, 2008

JON W. DUDAS  
*Director of the United States Patent and Trademark Office*